United States Patent [19]

Wuchinich

[11] 4,425,115
[45] Jan. 10, 1984

[54] ULTRASONIC RESONANT VIBRATOR

[76] Inventor: David G. Wuchinich, 116 Pinehurst Ave., New York, N.Y. 10033

[21] Appl. No.: 898,569

[22] Filed: Apr. 21, 1978

Related U.S. Application Data

[63] Continuation-in-part of Ser. No. 861,599, Dec. 19, 1977, Pat. No. 4,223,676, which is a continuation of Ser. No. 672,814, Apr. 1, 1976, Pat. No. 4,063,557.

[51] Int. Cl.³ .............................................. A61M 1/00
[52] U.S. Cl. .................................. 604/22; 128/303 R; 310/26
[58] Field of Search ................. 128/24 A, 276, 303 R; 32/DIG. 4; 310/26; 604/22

[56] References Cited

U.S. PATENT DOCUMENTS

| Re. 25,033 | 8/1961 | Balamuth et al. | 128/303 R |
| 2,723,386 | 11/1955 | Camp | 128/24 A |
| 3,113,225 | 12/1963 | Kleesattel et al. | 310/26 |
| 3,213,537 | 10/1965 | Balamuth et al. | 32/DIG. 4 |
| 3,375,583 | 4/1968 | Blank et al. | 128/24 A |
| 3,433,226 | 3/1969 | Boyd | 128/24 A |
| 3,589,363 | 6/1971 | Banko et al. | 128/276 |
| 3,693,613 | 9/1972 | Kelman | 128/24 A |
| 3,930,173 | 12/1975 | Banko | 310/26 |
| 4,063,557 | 12/1977 | Wuchinich et al. | 128/276 |
| 4,110,908 | 9/1978 | Cranston | 32/DIG. 4 |

*Primary Examiner*—Lee S. Cohen
*Attorney, Agent, or Firm*—Vorys, Sater, Seymour & Pease

[57] ABSTRACT

An ultrasonic resonant vibrator has a connecting portion connecting an ultrasonic vibration transducer to a tool which thereby ultrasonically vibrates at one end for fragmenting contacted tissue. The connecting portion is bifurcated by a slot, and a mount for mounting the vibrator in the handpiece is positioned toward the transducer from the slot. This structure is shaped, dimensioned and made of materials having acoustic properties such that there is only one node of ultrasonic vibrational movement between and including the slot and the mount and this node is spaced from the mount toward the slot to obtain increased ultrasonic vibration at the tissue-contacting end of the tool for better fragmenting a wider variety of tissues.

3 Claims, 3 Drawing Figures

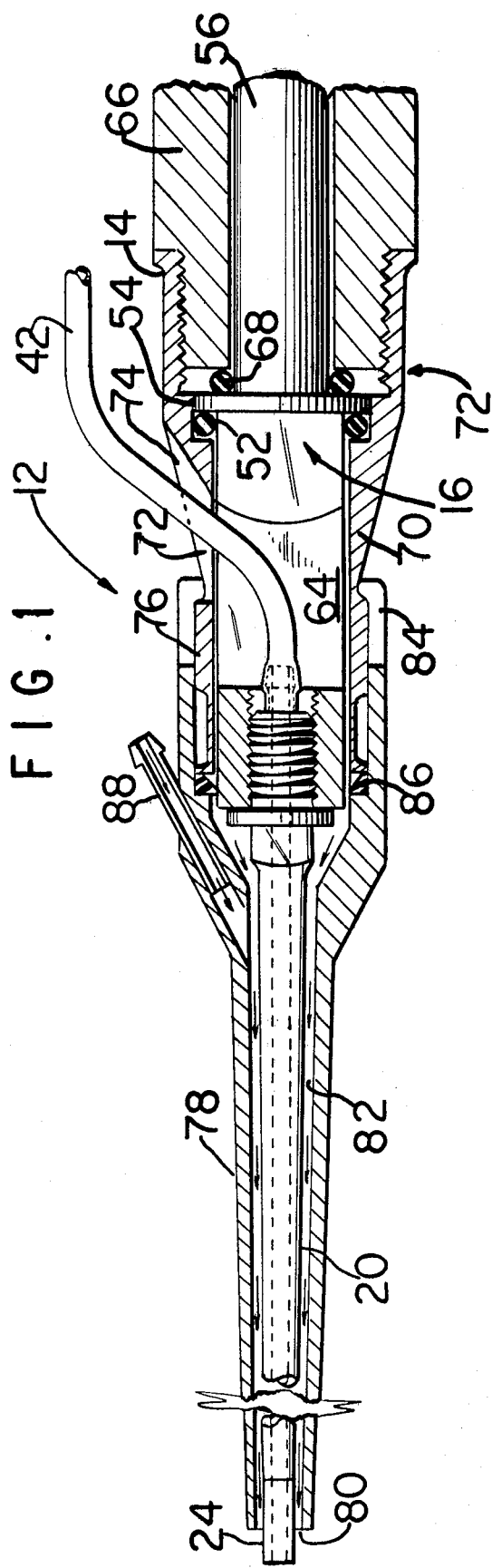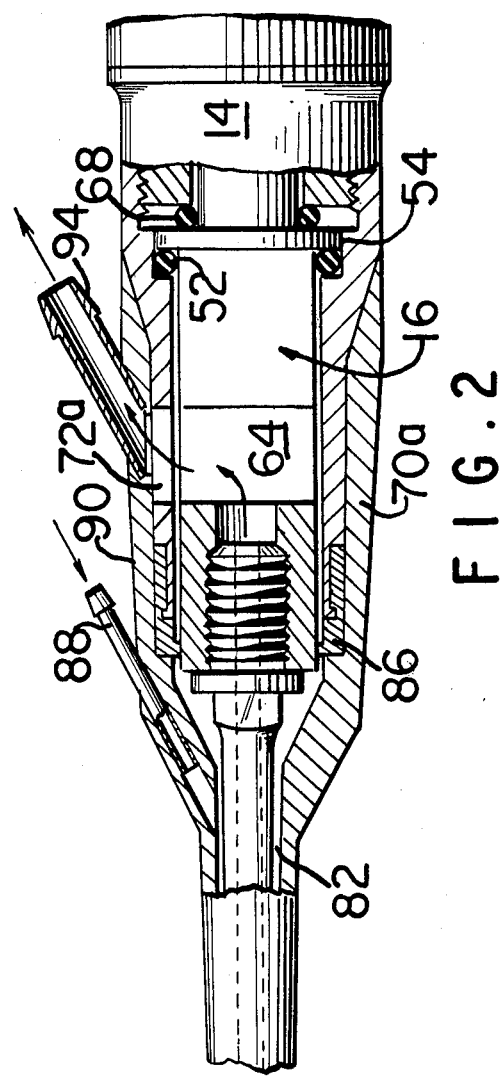

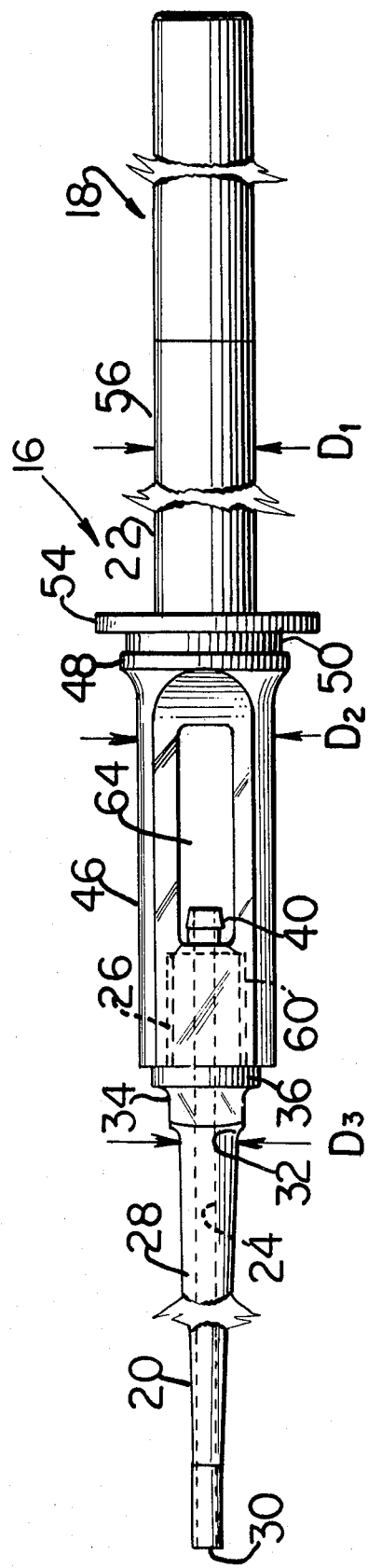

ULTRASONIC RESONANT VIBRATOR

BACKGROUND OF THE INVENTION

This application is a continuation-in-part of U.S. patent application Ser. No. 861,599 filed Dec. 19, 1977, now U.S. Pat. No. 4,223,676, which is a continuation of U.S. patent application Ser. No. 672,814 filed Apr. 1, 1976 and now U.S. Pat. No. 4,063,557.

This invention is directed to an apparatus for ultrasonically fragmenting and aspirating tissue in a surgical operation.

Ultrasonically vibrated surgical tools for removing various types of body tissues are well known. For example, certain of these instruments are commonly used in removing cataracts from the eye as illustrated by the assignee's U.S. Pat. No. 3,589,363 issued June 29, 1971 to A. Banko and C. D. Kelman. Another, the ultrasonic dental prophylaxis unit as illustrated by the assignee's U.S. Pat. No. 3,076,904 is a widely accepted and successful instrument for cleaning teeth. Other specialized ultrasonically driven surgical instruments have been patented, though the extent of their actual use by others is unknown.

The assignee, however, has several prior patents and patent applications which describe the use of ultrasonically vibrated tools to remove tissues. Among these are U.S. Pat. No. 4,016,882 issued Apr. 12, 1977, U.S. Pat. No. 3,526,219 issued Sept. 1, 1970, and U.S. Pat. No. 3,565,062 issued Feb. 23, 1971. None of the instruments shown in these patents, however, has been entirely satisfactory for removing all of the wide range of body tissues which have markedly different mechanical characteristics; i.e., compliance, ranging from liquid to a relatively hard and brittle material such as bone. Some tissues are therefore much more difficult to fragment than others and instruments built according to the patents have had difficulty providing sufficient ultrasonic vibration, and particularly sufficient stroke, to fragment effectively a wide enough variety of the tissues for its surgical use.

SUMMARY OF THE INVENTION

It is therefore an object of this invention to provide a novel surgical apparatus employing an effective ultrasonically vibrating tool.

Another object of the present invention is to provide an ultrasonically vibrating tool having aspiration means which are isolated from a connecting member's mounting fixtures.

Yet another object of the present invention is to provide ultrasonic surgical apparatus for fragmenting, and aspirating highly compliant tissue containing blood.

It is therefore also an object of this invention to provide apparatus for surgically removing tissue.

It is another object of this invention to provide apparatus for surgically disintegrating and aspirating tissue in an effective manner.

It is still another object of the present invention to provide surgical apparatus having an ultrasonically vibrating tool with a stroke of at least 5 mils (0.005 inch).

Still another object of this invention is to provide a high stroke ultrasonically vibrating surgical handpiece.

Another object of the present invention is to provide a conveniently held high power ulrasonic surgical tool having aspiration and irrigation.

Other objects and advantages of the present invention will be apparent to those skilled in the art from the description of the drawings and preferred embodiment.

To these ends, a novel surgical apparatus for fragmenting, and preferably aspirating, tissue is disclosed. The apparatus comprises an ultrasonic resonant vibrator dimensioned to be mounted in a handpiece and having an ultrasonic vibration transducer which is electrically excited from the handpiece for ultrasonic vibration and a tool having an end for fragmenting contacted tissue with ultrasonic vibration thereof. A connecting structure, which may be part of the tool but preferably is distinct therefrom to provide amplification of the ultrasonic vibration as later described in relation to a preferred embodiment, connects the tool to the transducer for vibrating the tool. It has a slot bifurcating the slotted portion of the connecting structure. A mounting arrangement for mounting the resonant vibrator in the handpiece is positioned along the resonant vibrator toward the transducer from the slot. This resonant vibrator structure is shaped, dimensioned and made of materials with acoustic properties in accordance with known design principles such that in the resulting unique structure there is one but only one node of ultrasonic vibratory motion between and including the slot and the mounting means which one node is spaced from the mounting means toward the slot.

It is well known in the design of ultrasonic resonant vibrators that the mount for supporting the vibrator should be at a node in the ultrasonic vibratory motion to avoid damping the ultrasonic vibration with the mount. It has now been discovered, however, that with the slotted, bifurcated structure described herein, increased ultrasonic vibration is obtained by designing the resonant vibrator with a node shifted from the mount toward the slot. The postulated theory for this otherwise surprising result is that the ultrasonic vibration at the bifurcation produces stresses which cause the bifurcated portions to vibrate transverse to the longitudinal axis of the resonant vibrator, which transverse vibrations are not transmitted to the tissue fragmenting end of the resonant vibrator and thus produce a loss in the vibration transmitted for use. The stresses producing the transverse vibration are then believed to decrease more rapidly than the vibration damping losses from shifting the node away from the mount increase so that net gain in ultrasonic vibration is achieved by designing the resonant vibrator with the node shifted from the mount toward the slot.

BRIEF DESCRIPTION OF THE DRAWINGS

FIG. 1 of the drawings is a sectional elevation of one version of the surgical handpiece according to this invention;

FIG. 2 is a sectional elevation of another version of the surgical handpiece; and FIG. 3 is a plan of the resonant vibrator employed in the handpiece of both FIGS. 1 and 2.

DESCRIPTION OF THE PREFERRED EMBODIMENT

The preferred embodiment is an improved apparatus for ultrasonically fragmenting and aspirating body tissue. The apparatus is embodied in a conveniently held handpiece 12, a cross-sectional view of which is shown in FIG. 1 of drawings, enclosing means for exciting a resonant member to vibrate in the ultrasonic range, including an aspirating tool vibrating at its tip in the ultrasonic frequency range at a longitudinal amplitude in excess of about 5 mils (0.005 inch).

To achieve such an effect in an instrument which can be conveniently held by a surgeon, a number of difficult obstacles must be overcome. One major obstacle is in transmitting excitation to an operating tool tip while at the same time such tip acts as the aspirating inlet to effect the surgical removal of the undesired tissue.

We have discovered that in order to surgically remove a broad enough range of compliant tissue that the surgeon is apt to encounter, an instrument which vibrates longitudinally in the range of at least 5 mils at about 25 KHz is necessary. At the same time as the tip is ultrasonically vibrating it is desirable to also apply aspiration to the affected tissue. A number of prior art issued patents such as previously mentioned do teach the application of aspiration together with an ultrasonic vibrating tool tip to remove body tissue. However, it has been found that except in specific instances where the particular tissue is readily susceptible to ultrasonic disintegration such as cataracts, it has been difficult to provide an ultrasonically vibrated tool to effectively remove tissue exhibiting a wide range of mechanical properties (i.e., compliance) which the surgeon may encounter in an operation. Thus, if the ultrasonic instrument was not adaptable to the range of tissue ordinarily encountered during specific types of operation, the instrument may have to be discarded for particular operations and is therefore an inconvenience during the operation. It is clearly recognized that to be acceptable to the surgeon, an instrument must be sufficiently rapid and selectively effective against the various types of tissue the surgeon is desirous of removing.

In particular, where highly compliant tissue mixed with blood is aspirated, there is the increased likelihood of occlusion of the aspiration conduit due to the coagulation of the blood. It is therefore desirable to provide as large an aspiration path as possible. This is to avoid clogging or occlusion of the aspiration path due to the increasing coagulation of the blood tissue mixture being aspirated. In addition, vibration apparently acts to increase the rate of coagulation. It is therefore additionally desirable that the aspiration path or conduit should preferably have minimal changes of direction of flow and where such changes are required, they should be as gentle as possible. Further pockets of low flow velocity are also to be avoided.

Referring to FIG. 1 of the drawings, the surgical instrument 12 is shown in sectional elevation and comprises a tubular handpiece 14 and an elongated resonant vibrator 16 inserted therein and projecting out of the front part of the handpiece. As the instrument is held and manipulated by the surgeon in one of his hands, the size and weight of the handpiece is limited by the ability of the hand to delicately grasp and manipulate the instrument. For this purpose, the outside diameter of the handpiece should not exceed about 1.5 inches (3.7 cm) in overall diameter and a diameter of about 1 inch (2.5 cm) is preferred.

Referring now to construction of the resonant vibrator 16, the vibrator is basically a mechanical vibrating system mounted in the handpiece. The vibrating system is divided into a transducer; i.e., a magnetostrictive stack composed of nickel alloy sandwich such as is taught in U.S. Pat. No. RE 25,033 and is well known in the art. Electrical oscillating current supplied to the winding of the coil induces mechanical oscillations in the stack, such oscillations being at the resonant frequency and having a maximum practical peak-to-peak stroke (amplitude) of about 1 thousandth of an inch (1 mil) at a frequency of about 25 KHz. As a practical matter due to limitations imposed by the state of the art, as frequency increases in the ultrasonic range, the stroke that one is able to obtain in the transducer is reduced.

However, it is well known in the art that if one desires to take the available stroke from the transducer and vary the stroke, an ultrasonic mechanical transformer may be used. The design of such a transformer which is fixedly attached to the transducer magnetostrictive stroke is taught, for instance, in the aforementioned U.S. Pat. No. RE 25,033.

Finally, the design of the transformer section must include and yield the preferred characteristics at the output portion of resonant vibrator. In this regard the output portion of the vibrator must vibrate ultrasonically with a desired stroke (peak to peak) of at least 0.005 inch (5 mils) while simultaneously functioning as an aspirator inlet. The output portion must also, for surgical requirements, be rather long and slender, while for aspiration purposes it is preferred to have as large a cross-sectional flow area as possible to thereby minimize the possibility of occluding the aspiration conduit.

Prior art hand-held commercial instruments, either providing irrigation or aspiration through the ultrasonic output end, have generally had strokes of less than 0.003 inch. Even this level of stroke is difficult to achieve at 25 KHz in a production instrument. The resonant vibrator output according to the present invention is (commercially) capable of producing a stroke in the range of at least 5 mils and preferably from 5 to 16 mils at about 25,000 cps.

An acceptable ultrasonically vibrated surgical handpiece capable of such an output; i.e., a stroke of at least 5 mils at 25 KHz, has not been achieved, whereas we have invented such as described herein.

FIG. 3 of the drawings illustrates a preferred version of the resonant vibrator 16 having the magnetostrictive stack 18 at one end, a tool 20 at the forward end, and a connecting member 22 intermediate the tool 20 and the stack 18. For purposes of description, the tool encompasses that portion of the vibrator having an aspiration conduit 24 axially located therethrough. The tool is also coincidentally a substantially unitary body, designed for replacement as required and attached to the connecting member by a male threaded insert 26 at its posterior end. The preferred tool comprises an elongated hollow tube 28 at its anterior end, being about 0.09 inch at its tip 30 with a uniform outside diameter for about 0.65 inch and then tapering uniformly to an outside diameter of about 0.14 inch over a length of about 2 inches to fillet 32, where it is machined into a hexagonal neck 34 of about 0.19 inch. The neck 34 is connected to a circular rim 36 of about 0.3 inch diameter and 0.05 inch thickness. From the rim 36, the previously described male threaded insert 26 which is aout ¼ inch long with an O.D. of about 0.21 inch, extends rearwardly and is chamfered at its end. The threaded insert 26 is necessarily a relatively large sized thread, being preferably a No. 12 screw thread, in order to withstand the extreme stresses present. Axially extending from the rearward end of the insert 26 is a nipple 40 having a neckedin outer surface for receiving and retaining an aspiration tube 42. The hollow aspiration conduit 24 extends the whole length of the tool and has a uniform internal diameter (I.D.) of preferably about 0.06 inch. Preferably the tool is made of a biologically compatible metal having a low characteristic acoustic impedance such as titanium or an alloy thereof.

The above-described tool 20, while susceptible to various modifications, necessarily must have an elongated tubular end having as small an outside diameter as is practical. Furthermore, since the tool tip 30 is to vibrate ultrasonically with a stroke in excess of 0.005 inch (5 mils), the tubular portion of the tool is tapered over most of its length to preferably reduce the stress to which the metal is subjected. Finally, and importantly, the tool in terms of its length and its distributed mass is dynamically a part of the resonant vibrator 16 which can magnify the 0.001 inch (1 mil) stroke input induced in the magnetostrictive stack 18 to in excess of a 5 mil output at the tool tip.

The connecting member 22 according to the present invention is a unitary metal structure also dynamically a part of a resonant vibrator which serves to connect the stack 18 to the tool 20 and, more importantly, to serve to transmit and modify the stroke as it is dynamically transmitted from the stack to the tool. Ideally the connecting member should be as wide as possible in contrast to the tool tip, as such a relative diameter increases the magnification, M, of the output stroke as much as possible at the tool tip in conformity with the following equation:

$$M = \sqrt{K_1 \frac{D_1^4}{D_2^4} + K_2 \frac{D_1^4}{D_3^4}}$$

where $K_1$ and $K_2$ are constants dependent on the lengths of the various elements and their material properties and $D_1$, $D_2$, and $D_3$ are the effective cross-sectional characters of the connecting member and tool as shown in FIG. 3 of the drawings. It is therefore readily apparent that the greater the diameter $D_1$ is in relation to diameters $D_2$ and $D_3$, the greater is the magnification M that is obtained. The node of motion of the resonant vibrator is located in the vicinity of flange 54, with the diameter $D_1$ of the connecting member being on the input side of the node and the diameters $D_2$ and $D_3$ being on the output side. But, as the portion 46 of the connecting member, which is defined by $D_2$ as the effective diameter, comprises the aspiration path communicating with the hollow tool, it is desirable to maintain the stroke level in this area as small as possible. If such connections are made, then the ratio of diameter $D_1$ to diameter $D_2$ should be as small as possible. Such a requirement modifies the above equation where if $D_2$ is made much larger than $D_1$, M becomes equal to $$\sqrt{K_2 \frac{D_1^4}{D_3^4}}$$

Thus the dynamic constraints appear to dictate a large diameter connecting member in order to achieve high magnification of output stroke. Since the handpiece 14 in which the vibrator and its connecting member are mounted has a practical limit to its size, it being necessary for the surgeon to conveniently hold it in one hand and manipulate it accurately, it has been previously found difficult to achieve high magnification in such small instrumentation.

To achieve such magnification, the connecting member 22 is made of a metal having a high characteristic acoustic impedance or an alloy such as monel shaped as shown and described herein. The anterior portion 46 of the connecting member 22 has a cross-section of about 0.38 inch square and a length of about 1.2 inches where it flares out to a circular rim 48 with a diameter of about 0.46 inch. The rim 48 forms the forward edge of an annular cutout 50 of about 0.435 inch diameter, which cutout 50 acts to retain for a first O-ring 52. The circular flange 54 serves as the rearward boundary of the cutout and functions to position the vibrator 16 in the handpiece 14 as will be hereafter described.

The rearward part of the connecting member is a solid circular rod 56 of about 0.28 inch in diameter and about 2 inches long, the posterior end of which is soldered, brazed, welded or otherwise fixed to the forward end of the magnetostrictive stack 18.

The anterior portion 46 of the connecting body has an axially located internally threaded bore 60 being sized to receive the full length of the male threaded insert 26 of the tool. The bore can have a shoulder against which the chamfered end of the threaded insert 26 stops under a predetermined torquing force. A large rectilinear slot 64 is located in the connecting member adjacent the end of the borehole and the tool's nipple extends into the opening formed by the slot. The aspiration tube 42, shown in FIG. 1, is thereby free to mate with the nipple in the opening thus formed by the slot without the necessity of a sharp radius being applied at the joint to either the aspiration tube or the conduit.

Referring again to FIGS. 1 and 2, where the resonant vibrator is shown mounted in the handpiece, the handpiece has a suitable wound coil (not shown) for exciting the magnetostrictive stack, and attached to a cable through which electrical power and signal conductors and cooling fluid are brought to the handpiece. The tubular part of the handpiece comprising a housing 80 has an opening through which the connecting member and stack are inserted. The housing 66 is undercut and externally threaded at its forward end. A second O-ring 68 is mounted on the rod 56 and is positioned between the housing's forward end and the flange 54 upon assembly of the handpiece.

The two O-rings 52 and 68 thus effectively seal the anterior portion of the connecting member forward of the flange from the internal volume of the handpiece enclosing the stack and containing the various electrical wiring and coolant supply lines in the handpiece.

A molded retainer 70 is positioned over the connecting member 22 and has an internally threaded cap 72 which is attached to the housing forward end. Internally forward of its cap, the retainer 70 is molded with a stepped internal diameter to fit over the first O-ring 52 in compressive contact and over the adjacent flange 54 with some minor clearance. The anterior portion of this stepped internal diameter is hexagonal in cross-section to enclose the anterior portion 46 of the connecting member, but with some minor clearance. Exteriorly the retainer 70 is molded with a dorsally located opening 74 through its wall adjacent the connecting member's slot. The opening 74 provides access for surgical grade plastic tubing 42 to connect to the tool nipple 40. The size of the opening and the slot is adequate so that the radius of curvature is gentle, thereby offering less resistance to aspirated blood containing tissue and lessening the possibility of occlusions occurring.

FIGS. 1 and 2 also illustrate two versions of an irrigation manifold 78, each version having a similar hollow truncated cone surrounding and spaced from the tool to provide an annular irrigation channel 82 having an annular nozzle 80 about ⅛ inch posterior to the tip of the tool. The flow of sterile irrigation fluid through the channel 82 has an effect on the tool output acting to dampen the vibration somewhat while importantly at the same time serving to cool the tool over most of its actual length.

The version of the manifold 78 illustrated in FIG. 1 widens posteriorly to fit over the retainer 70. The retainer in front of the opening 72 has a slightly larger outside width end depth, while the manifold's posterior end is molded with an interior lip 84. The manifold can therefore in assembly be slid over forward part of the retainer and when in proper assembled condition is held on the retainer by the lip 84.

The manifold 90 illlustrated in FIG. 2 has no lip but rather is tightly fitted over the retainer. The manifold in the second version has a smaller opening into which an aspiration pip 94 is inserted into the manifold's dorsal side and opens interiorly opposite the connecting member slot. The tool, though otherwise identical to that shown in FIGS. 1 and 2, is shown without its nipple. Aspirated material therefore flows from the hollow tool into the space provided by the slot 64 through an opening 70a in the retainer cap 72a and into the aspiration pipe 94.

An irrigation inlet pipe 88 is inserted fixedly into the cap's forward part and opened into the annular channel 82. Sterile surgical tubing (not shown) is connected to the irrigation as desired from a suitable source. A seal 86, preferably a silastic washer, is fitted over the anterior part of the connecting member adjacent a front edge of the retainer and serves to seal the irrigation fluid space from the space surrounding the connecting body (and serves as part of the aspiration fluid path in the handpiece shown in FIG. 2).

Supplying the irrigation fluid through the channel 82 provides three distinct advantages besides supplying irrigation fluid to the operative site. The irrigation fluid cools the vibrating tool and the material, blood, fluid and tissue being aspirated through the tool. If there is no such provision for cooling the high vibratory stroke output in excess of 0.005 inch of the tool would rapidly heat up from such intense vibration and weaken or damage the tool. Heat would also add to the rate of coagulation of blood being aspirated through the tool. Reducing the tool temperature thus reduces the possibility of occlusions. The irrigation fluid also wets the aspirated tissue, aiding in aspiration thereby. Further, it protects tissue not in contact with the tip.

The Nodal Position

As is well understood in the design of ultrasonic resonant vibrators of the general type shown in FIG. 3 for resonant ultrasonic vibration along the longitudinal axis thereof, the overall structure is shaped, dimensioned and made of materials having acoustic properties (as well as other desired properties) such that the whole has a length which is an integral multiple of one half the wavelength in its respective parts of the ultrasonic frequency at which it is resonant. This provides maximum ultrasonic stroke at the ends and at least one node of no ultrasonic vibration therebetween at which it is conventional practice, as before described, to provide a mount 50 for supporting the vibrator without damping the ultrasonic vibration. In specific example, the transducer 18 could be, in conventional practice, one half the resonant wavelength therein long, the portion 22 one quarter wavelength therein, and the rest to the free end 30 of the tool 20 another quarter wavelength therein so that a node occurs at the mount 50.

It has now been discovered, however, that increased ultrasonic vibration at the tissue contacting end 30 of the tool for the same input vibrational power can be obtained by redimensioning the structure shown in FIG. 3, while retaining the otherwise desired shape as shown in FIG. 3 and the acoustic properties of the materials (stainless steel which is acoustically similar to monel being, however, preferably substituted for the before described monel connecting member 16), so that the node is shifted toward the slot 64 which bifurcates the connecting member. This is believed to result from greater gains in damping transverse ultrasonic vibration into and out of the directions marked by diameter arrows $D_2$ in FIG. 3 in the bifurcated portions of the connecting member along slot 64 than damping losses at the mount 50 from the elastic O-rings 52, 68.

Specifically, the tool 20 is made of titanium about 3.2 inches from flange 54 to end 30 with a 0.25 inch hexagonal base, a 0.09 inch outside diameter end 30, and a 0.07 inch inside diameter aspiration conduit 24. The connecting member is made of stainless steel with an overall length of about 2.75 inches an outside diameter of about 0.54 inch in the portion 46, and a hollow portion 22 of an outside diameter of about 0.33 inch. The slot 64 is about 0.42 inch long and 0.16 inch wide. The rest of the structure is as before described, the resonant vibrator then having a somewhat reduced resonant frequency of about 23 kHz and a node approximately at the left end of the slot 64 as shown in FIG. 3. The vibration at the end 30 of the tool, however, is increased. In comparing the 23 kHz structure just described to the 25 kHz structure before described, vibrational velocities at the tool end 30 one and one-half times those of the 25 kHz structure for the same vibratory power are obtained, a dramatic 50% improvement.

In addition, the maximum stress in the vibrator is also reduced and distributed more gradually through the structure so that greater power can be applied without exceeding the strength limits of the structure. A gauge of this improvement called the Figure of Merit which is the vibrator gain divided by the maximum stress for the 23 kHz structure over the 25 kHz structure shows a 10% improvement to about 1.8 from about 1.6.

Although the invention has been described with reference only to redimensioning the structure shown in FIG. 3 to preserve the desired aspiration function of the long slot 64 and the amplification function of the different materials and diameters of the tool 20 and connecting member 16, it will be appreciated that changing the shape and acoustic properties of the various components could also shift the nodal position as described. Specifically, the tool and connecting member could be combined if amplification were not desired. These and other variations are contemplated as within the scope of the claimed invention.

I claim:
1. An ultrasonic resonant vibrator comprising:
an ultrasonic vibration transducer for external electrical excitation to vibrate at an ultrasonic frequency;
a tool having a free end for output ultrasonic vibration;
connecting means connecting the transducer to the tool for ultrasonically vibrating the tool with the vibrations from the transducer at the resonant fre- quency of the resonant vibrator, the connecting means having a slot bifurcating the connecting means; and mounting means spaced from the slot toward the transducer for supporting the resonant vibrator;

the combination of the transducer, connecting means, tool and mounting means defining the resonant vibrator and having the first node of the ultrasonic resonant vibrations from and including the mounting means toward the slot positioned away from the mounting means toward the slot, wherein said first node is positioned at a point where the gain in ultrasonic vibration at the end of the tool from positioning the first node toward the slot most exceeds the loss of ultrasonic vibration at the end of the tool from damping the vibration with the support of the resonant vibrator at the mounting means.

2. An ultrasonic resonant vibrator comprising:

an ultrasonic vibration transducer for external electrical excitation to vibrate at an ultrasonic frequency;

a tool having a free end for output ultrasonic vibration;

connecting means connecting the transducer to the tool for ultrasonically vibrating the tool with the vibrations from the transducer at the resonant frequency of the resonant vibrator, the connecting means having a slot bifurcating the connecting means; and mounting means spaced from the slot toward the transducer for supporting the resonant vibrator;

the combination of the transducer, connecting means, tool and mounting means defining the resonant vibrator and having the first node of the ultrasonic resonant vibrations from and including the mounting means toward the slot, positioned away from the mounting means toward the slot, wherein said first node is on a line normal to the longitudinal axis which intersects the longitudinal axis approximately at the end of the slot farthest from the mounting means.

3. An ultrasonic resonant vibrator dimensioned for mounting in a handpiece for fragmenting tissue contacted with an end thereof, the resonant vibrator comprising:

an ultrasonic vibration transducer for electrical excitation from the handpiece to vibrate at an ultrasonic frequency;

a tool having a free end defining the end of the resonant vibrator for ultrasonic vibration longitudinally of the tool to fragment contacted tissue;

a connecting member connecting the transducer to the other end of the tool for ultrasonically vibrating the free end of the tool, the connecting member having an elongated slot diametrically bifurcating the connecting member with the longitudinal axis of the slot coinciding with the longitudinal axis of the resonant vibrator; and mounting means spaced from the slot toward the transducer for mounting the resonant vibrator in the handpiece;

the combination of the transducer, connecting member, tool and mounting means defining the resonant vibrator with a longitudinal axis of each aligned along the longitudinal axis of the resonant vibrator, each being dimensioned along the longitudinal axis relative to the wavelength of the resonant frequency therein such that the resonant vibrator is an integral multiple of one half the wavelength of the resonant frequency long, and has one but only one node of the ultrasonic resonant motion between and including about the slot and the mounting means which one node is spaced from the mounting means toward the slot, wherein the resonant vibrator is further shaped, dimensioned and has acoustic properties such that it has a resonant frequency of about 23 kHz and the one node is positioned about at the end of the slot farthest from the mounting means.

* * * * *